United States Patent [19]

Winterton et al.

[11] Patent Number: 4,900,854

[45] Date of Patent: Feb. 13, 1990

[54] PROCESS FOR THE PREPARATION OF ASYMMETRICAL ALKALINE EARTH METAL ORGANOBORATES, ORGANOALUMINATES, ORGANOARSENATES, AND ORGANOPHOSPHATES

[75] Inventors: Richard C. Winterton; Ronald J. Hoffman; Thomas D. Gregory, all of Midland, Mich.

[73] Assignee: The Dow Chemical Company, Midland, Mich.

[21] Appl. No.: 281,427

[22] Filed: Dec. 8, 1988

Related U.S. Application Data

[63] Continuation-in-part of Ser. No. 29,124, Mar. 23, 1987, abandoned.

[51] Int. Cl.$^4$ .............................. C07F 9/72; C07F 9/50; C07F 5/02; C07F 5/06
[52] U.S. Cl. ....................................... 556/70; 556/170; 556/187; 568/6; 568/9; 568/17
[58] Field of Search .................. 556/70, 170, 187; 568/6, 9, 17

[56] References Cited

U.S. PATENT DOCUMENTS 4,349,483 9/1982 Beach .................................. 556/187

Primary Examiner—Michael L. Shippen
Attorney, Agent, or Firm—Andrew E. Pierce

[57] ABSTRACT

Process for the preparation of asymmetrical alkaline earth metal organoborates and organoaluminates represented by the formula I:

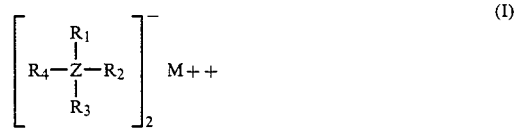

and asymmetrical alkaline earth metal organoarsenates and organophosphates represented by the formula II:

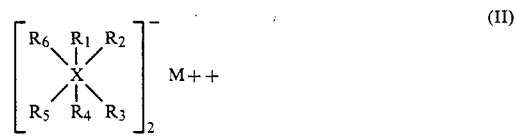

wherein Z is selected from the group consisting of boron and aluminum; X is selected from the group consisting of phosphorus and arsenic; M is an alkaline earth metal; and in which $R_1$–$R_6$ are independently selected from alkyl, aryl, alkaryl, aralkyl, alkenyl, cycloalkyl, and cyano with the proviso that $R_1$–$R_6$ are not all the same.

6 Claims, No Drawings

PROCESS FOR THE PREPARATION OF ASYMMETRICAL ALKALINE EARTH METAL ORGANOBORATES, ORGANOALUMINATES, ORGANOARSENATES, AND ORGANOPHOSPHATES

This application is a continuation-in-part of U.S. Ser. No. 029,124, filed Mar. 23, 1987, now abandoned.

BACKGROUND OF THE INVENTION

1. Field of the Invention

This invention relates to a process for the preparation of asymmetrical alkaline earth metal organoborates, organoaluminates, organoarsenates, and organophosphates.

2. Description of the Prior Art

Organoborates of the type $M(BR_3R')_n$ are relatively simple species to prepare. The usual route is to react a symmetrical borane, $BR_3$, with an organometallic reagent such as butyl lithium or dibutylmagnesium. The procedure to make compounds of the type $M(BR_2R'_2)_n$ is complicated by the fact that one of the starting materials must be an asymmetrical borane, $BR_2R'$. None of the methods known for accomplishing this result are commercially practical.

Klemann et al in U.S. Pat. No. 4,060,674 prepare alkali metal analogs of the asymmetrical alkaline earth metal organoborates and aluminates of the invention by reacting monoorganoalkali metal compounds with polyorganometallic compounds in an organic solvent.

Damico in J. Organic Chemistry, 29(7), 1971–1976 (1964) disclose the preparation of alkali metal analogs of the asymmetrical alkaline earth metal organoborates of the invention by reacting alkyl lithium and alkyl sodium with trialkyl boranes.

Malpass in U.S. Pat. No. 4,231,896 and U.S. Pat. No. 4,325,840 disclose the preparation of organomagnesium complexes of the formula:

$$(R'_2Mg)_m (RM)_n$$

wherein RM is an organoboron compound, R is a primary, secondary, or tertiary alkyl group, R' is a primary $C_1$–$C_{10}$ alkyl or phenyl group, or mixture thereof, and m and n are numbers such that the ratio of m over n is about 1 or greater. These complexes are prepared by reacting magnesium metal with a primary alkyl halide or aryl halide in the presence of a hydrocarbon solvent and, directly thereafter, adding an organoboron compound selected from the group consisting of trialkylboron, dialkylboron halide or alkylboron dihalides. Alternatively, the organoboron compound can be generated in situ by alkylation of a boron salt by the organomagnesium prepared by the above reaction of magnesium metal with a primary alkyl halide or aryl halide. The resultant organoboron compound then serves as a solubilizing agent for excess alkyl or aryl magnesium compound. The asymmetrical alkaline earth metal organoborates of Malpass are useful as components of electrolytes in electrochemical cells.

SUMMARY OF THE INVENTION

A process is disclosed for the preparation of asymmetrical alkaline earth metal organoborates, organoaluminates, organoarsenates, and organophosphates wherein said asymmetrical alkaline earth metal organoborates or organoaluminates have the formula:

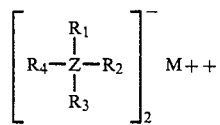

and said organoarsenates and organophosphates have the formula:

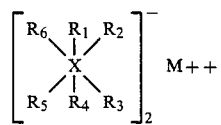

wherein Z is selected from the group consisting of boron and aluminum, X is selected from the group consisting of arsenic and phosphorus, M is an alkaline earth metal, and $R_1$–$R_6$ are independently selected from alkyl, aryl, alkaryl, aralkyl, alkenyl, cycloalkyl, and cyano.

The alkaline earth metal organoborates and organoaluminates of the invention are prepared by the process of:

(1) reacting an organohaloboron or an organohaloaluminum of the formula:

$$Z(R)_2W$$

with (2) an organoalkaline earth metal compound of the formula:

$$M(R')_2$$

wherein Z is as defined above, R and R' are as defined above for $R_1$–$R_6$ with the proviso that R and R' are not the same, and W is halogen.

The alkaline earth metal organoarsenates and organophosphates of the invention are prepared by the process of:

(1) reacting an organohaloarsorane or organohalophosorane of the formula:

$$X(R)_4W$$

(2) an organoalkaline earth metal compound of the formula:

$$M(R')_2$$

wherein X is as defined above, R and R' are as defined above for $R_1$–$R_6$ with the proviso that R and R' are not the same, and wherein W is halogen. The compounds of the invention are useful as components of electrolytes in electrochemical cells, as described in copending application, Ser. No. 936,531, filed Dec. 1, 1986, incorporated herein by reference.

DETAILED DESCRIPTION OF THE INVENTION AND THE PREFERRED EMBODIMENTS

The present invention relates to a process for the preparation of asymmetrical alkaline earth metal organoborates and organoaluminates or organoarsenates, and organophosphates having respectively formulas I and II.

These compounds are prepared by reacting an organo alkaline earth metal compound, i.e., organomagnesium, with an organohaloboron, -aluminum, -arsorane, or -phosphorane. The desired asymmetrical alkaline earth metal compounds are prepared by reacting an organo alkaline earth metal compound having organo groups which are different from the organo groups in the organohaloboron, -aluminum, -phosphorane, or -arsorane. The reaction is conducted at ambient temperature and pressure in an organic solvent or mixture thereof under an inert atmosphere. All solvents used were purified by distillation from molten alkali metal and alkali metal ketyls.

The following examples illustrate the various aspects of the invention but are not intended to limit its scope. Where not otherwise specified throughout this specification and claims, temperatures are given in degrees centigrade and parts, percentages, and proportions are by weight.

EXAMPLE 1

Magnesium dibutyldiphenylborate was prepared as follows:

Bromodiphenylborane was dissolved in the amount of 7.4 milliliters (40 millimoles) in 40 milliliters of tetrahydrofuran in the following manner: The bromodiphenylborane was cooled to $-78°$ C. and tetrahydrofuran was added. On warming, a reaction took place producing a solid tetrahydrofuran/bromodiphenylborane adduct. This product dissolves as the solution warms further toward room temperature, with stirring, yielding a clear solution. Thereafter, 56.3 milliliters of 0.71 molar dibutylmagnesium in hexane was added after first cooling the diphenylbromoborate solution to $-78°$ C. in a dry ice/acetone bath. The reaction mixture was allowed to warm slowly to room temperature with stirring. Stirring was continued for one hour. The solvent was evaporated by distillation under reduced pressure and the residue was redissolved in 25 milliliters of tetrahydrofuran. Thereafter, 20 milliliters of 1,4-dioxane were added and the mixture was stirred for over 30 minutes. Substantial amounts of a white precipitate had formed after this time. The mixture was decanted onto a "fine" fritted glass filter. The filtrate was collected by drawing it through the frit with a partial vacuum.

As the filtrate collected, two phases formed which had not been apparent in the initial suspension. In addition, roughly 60% of the initial precipitate redissolved. NMR and chemical analysis of the two liquid phases indicated that the bottom layer was primarily the desired product. However, it could not be isolated directly. On stirring the two phases overnight, a precipitate again appeared. The solid remaining on the frit was analyzed and found to be approximately 60% $MgBr_2-C_4H_8O_2$. This was extracted with tetrahydrofuran containing 10 volume percent of dioxane. The extract was combined with the earlier filtrate and evaporated to dryness. The resulting powders were washed with hexane and again extracted with tetrahydrofuran containing 25 volume percent of 1,4-dioxane and filtered. The powders were finally dried. NMR analysis indicated a butyl-to-phenyl ratio of 1:1. Chemical analysis indicated that the final powder was greater than 91% $[(Ph_2Bu_2)B]_2$ Mg and less than 8.8% by weight of $MgBr_2-C_4H_8O_2$. NMR analysis also indicated that six molecules of tetrahydrofuran were bound to the magnesium borate species as a solvate.

EXAMPLE 2

Magnesium dibutyldiphenylaluminate is prepared as follows:

Bromodiphenylaluminum (10.6 grams, 40 millimoles) is dissolved in 40 milliliters of tetrahydrofuran after first cooling in a dry-ice/acetone bath and warming slowly. Thereafter, 56.3 milliliters of 0.71 molar dibutylmagnesium in hexane is added with stirring and cooling to $-78°$ C. The mixture is stirred for 30 minues and allowed to warm to room temperature. The by-product, magnesium bromide, is precipitated with 1,4-dioxane and separated by filtration. The final product, magnesium dibutyl-diphenylaluminate, is washed with hexane and purified, if necessary.

EXAMPLE 3

Magnesium dibutyltetraphenylarsenate is prepared as follows:

Chlorotetraphenyl arsorane (16.35 grams, 40 millimoles) is dissolved in 40 milliliters of tetrahydrofuran which has been cooled in a dry-ice/acetone bath. After warming, a clear solution of the arsorane results. 56.3 milliliters of 0.71 molar dibutylmagnesium is then added after first cooling the reaction mixture to $-78°$ C. After slowly warming to room temperature the solvents are evaporated and the residue is extracted with tetrahydrofuran. The by-product, magnesium chloride, is precipitated with 1,4-dioxane and collected on a fritted glass filter. The filtrate is evaporated to dryness under vacuum and the residue, magnesium dibutyltetraphenylarsenate, is washed with hexane and further purified, if necessary.

EXAMPLE 4

Magnesium dibutyltetraphenylphosphate is prepared as follows:

Bromotetraphenyl phosphorane (16.77 grams, 40 millimoles) is dissolved in 40 milliliters of tetrahydrofuran which has been cooled in a dry-ice/acetone bath. After warming, a clear solution of the phosphorane results. 56.3 milliliters of 0.71 molar dibutylmagnesium is then added after first cooling the reaction to $-78°$ C. After slowly warming to room temperature the solvents are evaporated and the residue is extracted with tetrahydrofuran. This by-product, magnesium bromide, is precipitated with 1,4-dioxane and collected on a fritted glass filter. The filtrate is evaporated to dryness under vacuum and the residue, magnesium dibutyltetraphenylphosphate, is washed with hexane and further purified, if necessary.

While this invention has been described with reference to certain embodiments, it will be recognized by those skilled in the art that many variations are possible without departing from the spirit and scope of the invention and it will be understood that it is intended to cover all changes and modifications of the invention disclosed herein for the purposes of illustration which do not constitute departure from the spirit and scope of the invention.

The embodiments of the invention in which an exclusive property or privilege is claimed are defined as follows:

1. A process for preparing an asymmetrical alkaline earth metal organoborate or aluminate of the formula:

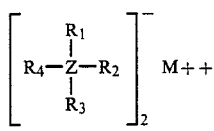 (I)

wherein Z is selected from the group consisting of boron and aluminum, M is an alkaline earth metal, and $R_1$–$R_4$ are independently selected from alkyl, aryl, alkaryl, aralkyl, alkenyl, cycloalkyl, and cyano by the steps of:

(1) reacting an organohaloboron or organohaloaluminum of the formula:

$Z(R)_2W$ with (2) an organoalkaline earth metal compound of the formula:

$M(R')_2$ wherein Z is as defined above, R and R' are as defined above for $R_1$–$R_4$ with the proviso that R and R' are not the same, and W is halogen.

2. A process for preparing an asymmetrical alkaline earth metal organoarsenate or organophosphate of the formula:

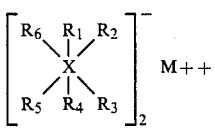 (II)

wherein X is selected from the group consisting of arsenic and phosphorus, M is an alkaline earth metal, and $R_1$–$R_6$ are independently selected from alkyl, aryl, alkaryl, aralkyl, alkenyl, cycloalkyl, and cyano by the steps of:

(1) reacting an organohaloarsorane or organohalophosphorane of the formula:

$X(R)_4W$ with (2) an organoalkaline earth metal compound of the formula:

$M(R')_2$ wherein X and R are as defined above, R and R' are as defined above for $R_1$–$R_6$ with the proviso that R and R' are not the same, and wherein W is halogen.

3. The process of claim 1 wherein R is aryl and R' is alkyl.

4. The process of claim 3 wherein R is phenyl and R' is butyl.

5. The process of claim 2 wherein R is aryl and R' is alkyl.

6. The process of claim 5 wherein R is phenyl and R' is butyl.

* * * * *